United States Patent
Beacham et al.

(10) Patent No.: US 9,987,809 B2
(45) Date of Patent: Jun. 5, 2018

(54) SYSTEM AND METHOD FOR MANUFACTURING AN ULTRASOUND PROBE LENS

(71) Applicant: GENERAL ELECTRIC COMPANY, Schenectady, NY (US)

(72) Inventors: Jimmie Autrey Beacham, West Allis, WI (US); Jessica Lynn Abraham, Chandler, AZ (US); Brian John Masterson, Delafield, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 629 days.

(21) Appl. No.: 14/587,103

(22) Filed: Dec. 31, 2014

(65) Prior Publication Data

US 2016/0185056 A1 Jun. 30, 2016

(51) Int. Cl.
| | |
|---|---|
| *B29D 11/00* | (2006.01) |
| *B33Y 80/00* | (2015.01) |
| *B33Y 50/00* | (2015.01) |
| *A61B 8/00* | (2006.01) |

(52) U.S. Cl.
CPC .... *B29D 11/0099* (2013.01); *B29D 11/00009* (2013.01); *B29D 11/00807* (2013.01); *B29D 11/00961* (2013.01); *B33Y 50/00* (2014.12); *B33Y 80/00* (2014.12); *A61B 8/4483* (2013.01)

(58) Field of Classification Search
CPC ........ B29D 11/00951; B29D 11/00961; B29D 11/0098; B29D 11/0099
See application file for complete search history.

(56) References Cited

U.S. PATENT DOCUMENTS

| | | | |
|---|---|---|---|
| 2006/0154075 A1* | 7/2006 | Kuniyasu | B06B 1/064 428/411.1 |
| 2007/0016048 A1* | 1/2007 | Baba | G01S 15/8925 600/447 |
| 2016/0287909 A1* | 10/2016 | Maxwell | A61N 7/02 |

FOREIGN PATENT DOCUMENTS

WO 2013166019 A1 11/2013

* cited by examiner

*Primary Examiner* — Lisa L Herring
(74) *Attorney, Agent, or Firm* — Grogan, Tuccillo & Vanderleeden, LLP

(57) ABSTRACT

A method includes the steps of measuring a surface profile of a first component, determining a profile of a second component, the profile of the second component being configured to correspond to the surface profile of the first component, and manufacturing the second component utilizing additive technology in accordance with the determined profile.

7 Claims, 5 Drawing Sheets

SYSTEM AND METHOD FOR MANUFACTURING AN ULTRASOUND PROBE LENS

TECHNICAL FIELD

Embodiments of the invention relate generally to adaptive manufacturing and additive technology and, more specifically, to a system and method for manufacturing an ultrasound probe lens utilize a combination of adaptive manufacturing and additive technology.

DISCUSSION OF ART

Ultrasonic diagnostic imaging systems allow medical professionals to examine internal structures of patients without invasive exploratory surgery. Ultrasonic diagnostic imaging systems typically include a transducer probe connected to a host system that provides control signals to the probe, processes data acquired by the probe, and displays a corresponding image.

Existing transducer probes generally include a row of transducer elements, each of which is connected to a terminal of a transducer control assembly or application specific integrated circuit (ASIC) that processes signals transmitted to and received from the acoustic elements. In some ultrasound transducer architectures, it is necessary to utilize a lens or lenses to focus the reverberating sound signals to the piezoelectric array of pixels on the surface of the transducer elements. These lenses are typically made from a polymeric material requiring a tightly toleranced curvature in one or more directions. Known methods for manufacturing these lenses typically involve a molding technique that forms a lens with a room temperature vulcanization (RTV) material, or applying a "boot" or net shape molded polymer cover on top of the transducer assembly. As will be readily, appreciated, both of these techniques rely on a near perfect stack up of the transducer components below, including z-axis height and parallelism. To better control alignment, very tight tolerances on machined parts to which the transducer is assembled are required.

In particular, current transducer processing requires the lamination of individually processed layers. As a result, each transducer may have a range of variation in mechanical stack-up, alignment and planarity as a result of the properties of the various layers of components. It is expected that future probe designs requiring the tiling of multiple transducers, both linear and curved, will be subject to even more part to part, and intra-part, variation, thereby increasing the challenge of maintaining the alignment (x, y and z) necessary to provide adequate performance using a single dimensioned lens made in a conventional manner. It is anticipated, therefore, that this will drive the design of the transducer and the other components of the probe to be within extremely tight tolerances to minimize alignment error.

In view of the above, there is therefore a need for a system and method for manufacturing an ultrasound transducer lens that enlarges the necessary assembly tolerances for the transducer while ensuring adequate performance.

BRIEF DESCRIPTION

In an embodiment, a method for additive manufacturing is provided. The method includes the steps of measuring a surface profile of a first component, determining a profile of a second component, the profile of the second component being configured to correspond to the surface profile of the first component, and manufacturing the second component utilizing additive technology in accordance with the determined profile.

In an embodiment, a method of manufacturing a lens for an ultrasound probe is provided. The method includes the steps of measuring a surface profile of an acoustic stack of the probe, calculating a profile for the lens, and printing the lens onto the acoustic stack in accordance with the calculated profile.

In an embodiment, a system for manufacturing an ultrasound probe is provided. The system includes a laser mapping device configured to measure a surface profile of a transducer of the probe, a data analyzer configured to receive surface profile data from the laser mapping device and to calculate a profile for an acoustic lens in dependence upon the surface profile data, and an additive printing device configured to print an acoustic lens on the transducer in accordance with the calculated profile.

In another embodiment, a method of manufacturing a lens for an ultrasound probe is provided. The method includes the steps of mapping a surface profile of a transducer of the ultrasound probe, determining a profile of the lens, the profile of the lens being configured to correspond to the surface profile of the transducer, manufacturing a mold having a mold profile corresponding to the determined profile of the lens, introducing a liquid material into the mold, submerging the transducer of the ultrasound probe in the liquid material, allowing the liquid material to cure to form the lens and removing the ultrasound probe and lens from the mold.

In yet another embodiment, a method of manufacturing a lens for an ultrasound probe is provided. The method includes the steps of measuring a surface profile of a transducer of the ultrasound probe, determining a profile of the lens, the profile of the lens being configured to correspond to the surface profile of the transducer, printing the lens on a substrate utilizing additive technology in accordance with the determined profile, removing the substrate from the lens, tacking the lens to the transducer of the ultrasound probe, over-molding the lens and the transducer with a curable material to bond the lens in place.

DRAWINGS

The present invention will be better understood from reading the following description of non-limiting embodiments, with reference to the attached drawings, wherein below:

DETAILED DESCRIPTION

Figure 1:
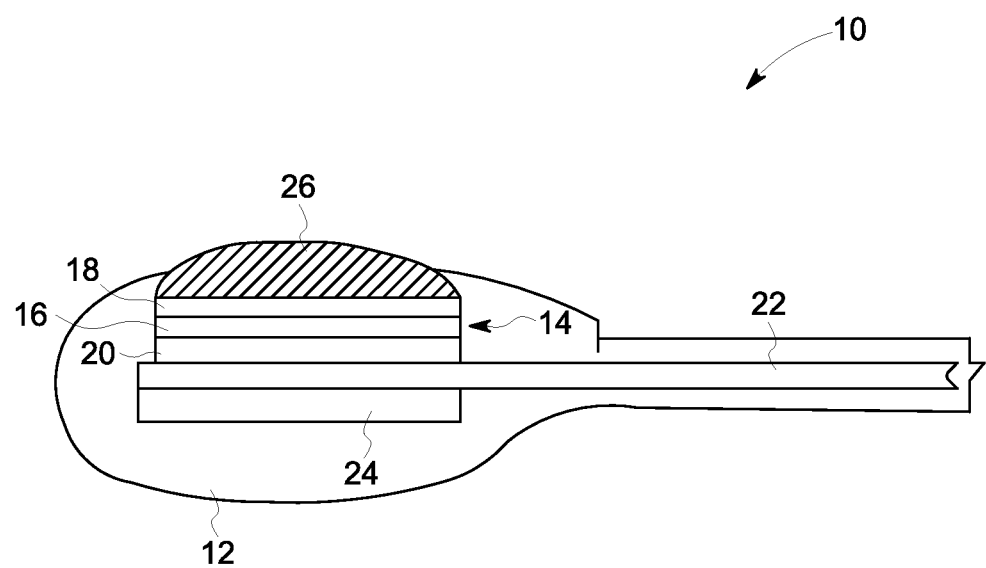
FIG. 1 is a cross-sectional, side view of an ultrasound probe in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts. Although embodiments of the present invention are described as intended for use with interconnected medical devices and interfaces, it will be appreciated that embodiments may be adapted for use in connection with interconnected electrical devices, more generally. While the embodiments described below are directed to the manufacturing of an ultrasound probe lens utilizing additive technology, the present invention is not intended to be so limited in this regard. In particular, the present invention may be adapted to provide for the manufacturing of various components and structures utilizing additive technology, in addition to ultrasound probe lenses. As used herein, "additive technology" or "additive manufacturing" means a process used to make a three-dimensional object, in which successive layers of material are laid down under computer control.

Figure 2:
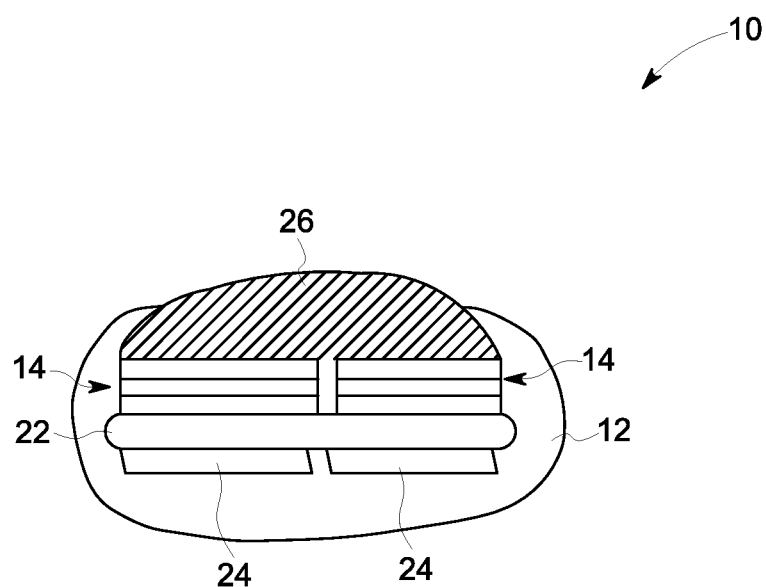
FIG. 2 is a cross-sectional, end view of the ultrasound probe of FIG. 1.

Referring now to FIGS. 1 and 2, an ultrasound probe 10 is illustrated. The ultrasound probe 10 may be of the type generally known in the art and includes a housing 12 having an acoustic stack 14 disposed therein. The acoustic stack 14 may include an array of first components, such as transducer elements 16, a matching layer 18 and a dematching or backing layer 20, as is known in the art. As also shown therein, the probe 10 may also include a flex-cable 22 and an ASIC 24. The transducer elements 16 are connected to the ASIC, which processes signals transmitted to and received from the transducer elements 16. Typically, such connections are made by soldering wires disposed at one end of the flex-cable 22 to the individual transducer elements 16. The other end of the cable 22 is generally connected to a console with all the signal processing electronics. Typically, an ultrasound probe contains hundreds of transducer elements arranged at varying pitches.

As also shown in FIGS. 1 and 2, the ultrasound probe 10 includes a second component, such as lens 26, that covers the acoustic stack 14 and the array of transducer elements 16, which serves to focus the energy emitted by the array. In an embodiment, the lens 26 is a custom polymer lens formed by additive manufacturing such as, for example, 3D printing, as discussed in detail hereinafter.

Figure 3:
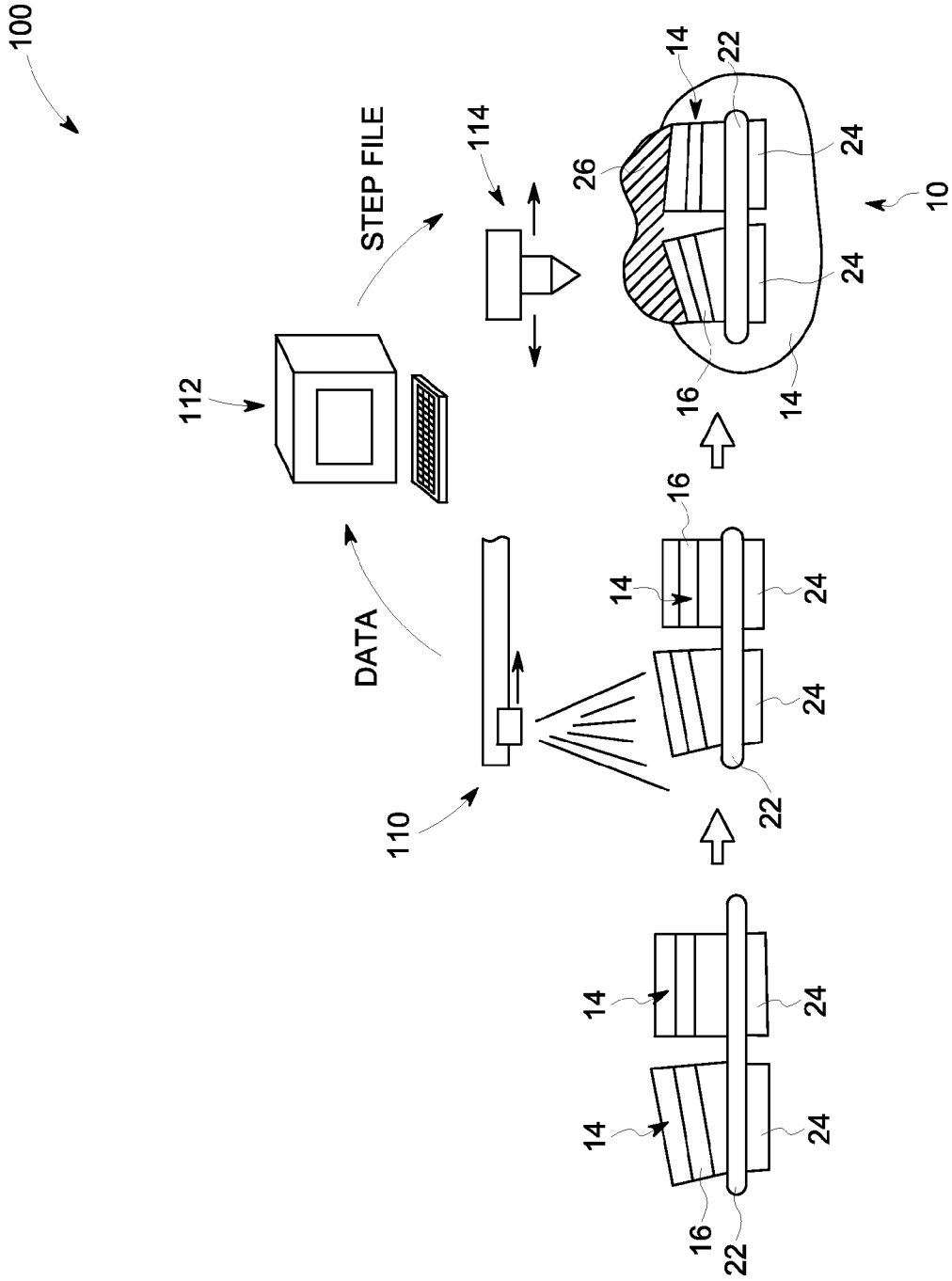
FIG. 3 is a schematic illustration of a system for manufacturing an ultrasound probe lens in accordance with an embodiment of the present invention.

With reference to FIG. 3, a system 100 for manufacturing the custom lens 26 for the ultrasound probe 10 is illustrated. As illustrated therein, the system 100 includes a laser mapping device 110, a data analyzer 112 and an additive manufacturing device 114. The laser mapping device 110 may be a laser surface profilometer, or any type of laser mapping or scanning device known in the art. The laser mapping device 110 is configured to measure and map the surface profile of the transducers 16 of the acoustic stacks 14 of the probe. As used herein, "surface profile" means the topography of the acoustic stack 14, including any variation of the acoustic stack in the x, y and z planes, as well as any rotation around the x, y and z axes. Topography or surface profile data gathered by the laser mapping/scanning device 110 may then be sent to the data analyze 112 for processing. In addition, the laser mapping device 110 is configured to scan and/or map the lens 26 of the transducer probe 10 once the lens is manufactured, to verify the that the contour of the lens is acceptable, as discussed in detail below.

In an embodiment, the data analyzer 112 may be a personal computer or other processor-based or micro-processor based system including system including systems using microcontrollers, reduced instruction set computers (RISC), ASICs, logic circuits, and any other circuit or processor capable of executing the functions described herein. These examples are exemplary only, and thus are not intended to limit in any way the definition and/or meaning of the term "computer." The computer or processor executes a set of instructions that are stored in one or more storage elements, in order to process input data. The storage elements may also store data or other information as desired or needed. The storage element may be in the form of an information source or a physical memory element within a processing machine. The set of instructions may include various commands that instruct the computer or processor as a processing machine to perform specific operations, as discussed hereinafter.

The data analyzer 112 is configured to receive the surface profile data gathered by the laser mapping device 110 and to process the data to calculate tolerance error in the acoustic stack 14. This can then be fed to a model whereby the data analyzer 112 may calculate the ideal curvature of the lens 26 for each individual probe 10 such that the lens 26 closely corresponds to the surface profile of the transducers. As used herein, "correspond to" means that the surface profile of one component closely mirrors the surface profile of another component, such that one component contains a negative impression of the surface profile of the other component. Moreover, the data analyzer 112 is configured to convert the model into a step file or other file format that can be used by the additive manufacturing device 114, and to relay the step file to the additive manufacturing device 114.

In an embodiment, the additive manufacturing device 114 may be a 3D printing device of the type generally known in the art. The device 114 is configured to releasably and securely receive the probe housing 12 having an array of transducers (defining the acoustic stacks 14) disposed therein, and to align the probe 10 therein. Once the device 114 is configured and the probe 10 is properly aligned, the device 114 may print the lens 26 on the acoustic stack 14 in dependence upon the measured surface profile of the transducers 16 and/or acoustic stack 14.

Figure 4:
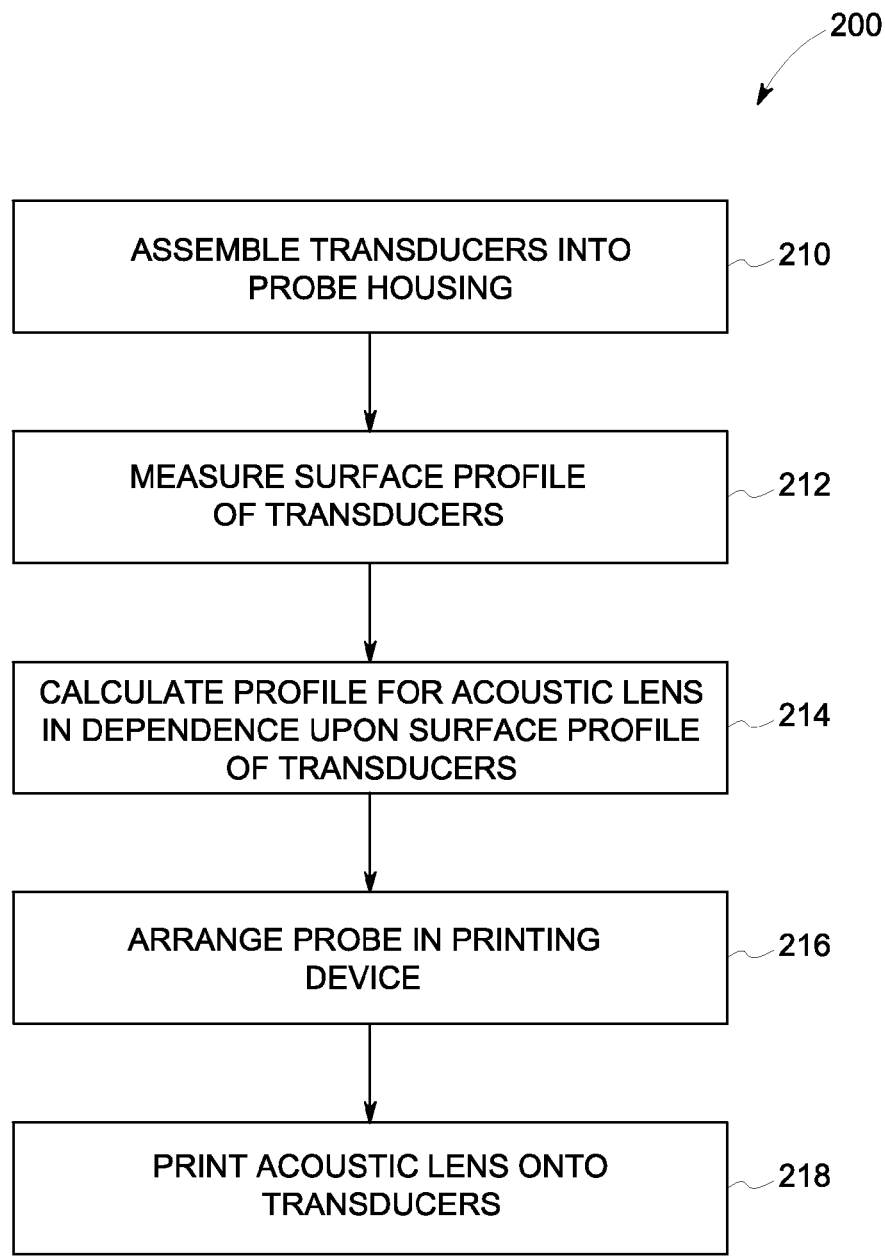
FIG. 4 is flow diagram illustrating a method of manufacturing an ultrasound probe lens in accordance with an embodiment of the present invention.

With reference to FIG. 4, a method 200 of manufacturing an ultrasound probe 10 is provided. In an embodiment, the transducers 16 (defining the acoustic stack 14), housing 12, ASIC 24 and flex-cable 22 may be assembled in any conventional manner known in the art. In particular, at step 210 an array of transducers are assembled into the housing 10. Once the transducer array is constructed and assembly into the housing 12, the surface profile of the transducers 16 (i.e., the acoustic stack 14) is measured relative to a datum on the housing 12, at step 212. In an embodiment, the surface profile may be measured using a 3D laser scanning system or device of the type known in the art to capture any variation of the acoustic stack 14 in the x, y and z planes and/or any rotation about the x, y and z axes. In an embodiment, other methods known in the art may also be utilized to map the surface profile of the acoustic stack 14 without departing from the broader aspects of the present invention. The measured surface profile data is then transmitted to a data analyzer for storage and processing. In an embodiment, the data analyzer may be a general purpose computer operating according to a pre-programmed set of instructions, as discussed above. In particular, at step 214, the surface profile data is processed by the computer to calculate tolerance error, which is then fed to a model that calculates the optimum or ideal curvature or contour of the lens for that specific transducer assembly. At step 216, once the desired curvature or contour for the lens is determined, the transducer assembly is fixture inside a 3D printing device where initial alignment and calibration may be performed. Once the 3D printing device is configured, printing of the custom, polymer lens having the curvature or contour previously determined is initiated, at step 218. After the custom lens is printed, the contour of the lens is verified to ensure it is within established tolerances and in accordance with the what had been calculated. In an embodiment, this verification step may be carried out utilizing the same 3D laser scanning system utilized to measure the surface profile of the transducer array/acoustic stack. In other embodiments, other measuring and imaging systems known in the art may also be utilized to verify the contour of the lens.

As will be readily appreciated, the concept of adaptive manufacturing using 3D printing allows for measurement of the surface profile of the transducers, which can then be used to compute the ideal shape of a lens and to print that specific profile onto the surface of the pixelated array. The system and method of the present invention, therefore, opens necessary assembly tolerances for the transducers and leverages the feedback loop of the laser mapping device; the system and method, therefore, provides for an essentially custom fit polymer lens for each transducer probe. Indeed, utilizing additive technology (i.e., 3D polymer printing) to manufacture the lens allows for the relaxation of transducer and subcomponent tolerances.

In addition, utilizing the assembly data in real time to make a compensating lens obviates the need to use costly machine parts and increases yield. Moreover, the system and method of the present invention reduces the amount of software correction and calibration needed at the probe and system level by correcting the errors at the transducer level with a customized lens. Indeed, existing methods of manufacturing ultrasound probes require each component to be within very tight tolerances to eliminate or reduce stack-up issues in the probe, as a whole. With the present invention, however, any stack-up issues may not have to be addressed during the manufacturing of each subcomponent, i.e. at each step in the manufacturing process, but can instead be addressed in aggregate, in a single step, when printing the custom lens. This leads to an ease of manufacturing, a reduction in cost and a more predictable build cycle of the probe that may translate to higher performance and custom satisfaction.

In addition to the above, the system and method of manufacturing a lens for an ultrasound probe utilizing additive technology may drive higher image quality, open the design space for complex geometry ultrasound probes requiring tiling, and allow for more ergonomic designs for patient contact. In particular, the use of 3D printing to manufacture custom ultrasound probe lenses can open up the types of materials to be considered for lenses.

Moreover, the present invention may also lead to improved serviceability of ultrasound probes. In particular, if an ultrasound probe ever requires a new lens because, for example, the lens has been damaged, the profile data for that particular probe could be retrieved from a central database and a new lens can be printed to replace the damaged one. It is contemplated that such replacement of damaged lens by additive printing can take place at designated service centers, obviating the need to ship probes all over the world for repair, which may likewise translate into lower costs.

Figure 5:
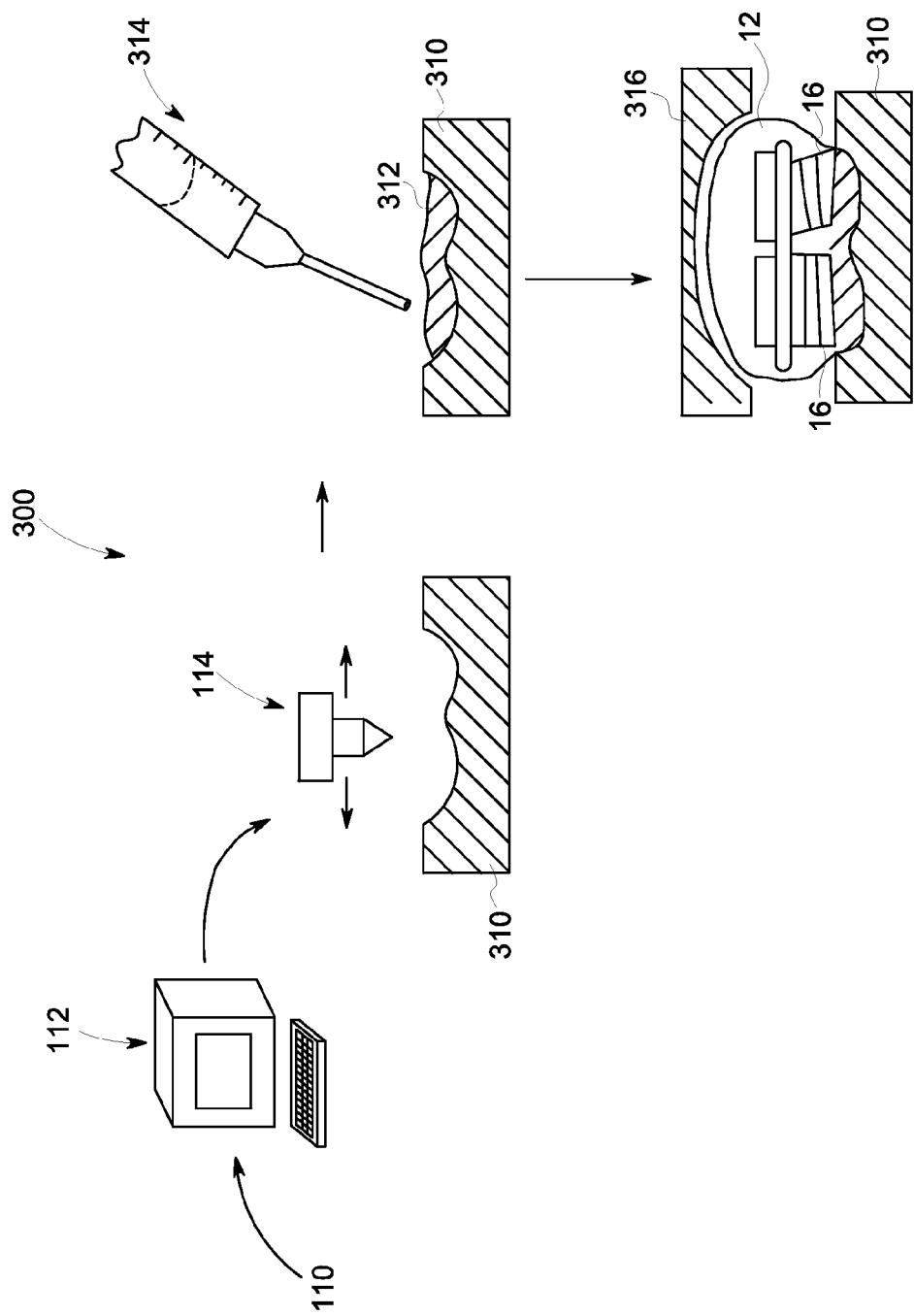
FIG. 5 is a schematic illustration of a system for manufacturing an ultrasound probe lens in accordance with another embodiment of the present invention.

With reference to FIG. 5, a system 300 for manufacturing the custom lens 26 for the ultrasound probe 10 according to another embodiment of the present invention is illustrated. Like the system 100 described above, system 300 includes a laser mapping device 110, a data analyzer 112 and an additive manufacturing device 114. As described above, the laser mapping device 110 is configured to measure and map the surface profile of the transducers 16 of the acoustics 14 of the probe 10. The data analyzer 112 is configured to receive the surface profile data gathered by the laser mapping device 110 and to calculate the ideal curvature of the lens 26 for each probe 10 in the manner hereinbefore described. Rather than printing the lens 26 as discussed above in connection with FIGS. 3 and 4, however, the additive manufacturing device 114 of the system 300 is configured to create a mold 310 customized for each transducer in dependence upon the lens curvature calculated by the data analyzer 26. In an embodiment, the mold 310 may be a fused disposition material or PolyJet® disposable mold. As will be readily appreciated, the additive manufacturing device 114 creates a mold 310 that mirrors the curvature of the lens 26 to be created. As further shown in FIG. 5, once the mold 310 is produced, lens material 312 in liquid form may be introduced into the mold 210 by an injection device 314.

As also show in FIG. 5, once the lens material 312 is injected into the mold 310, the transducers 15, already assembled into the housing 12, are clamped into a clamp 316 and lowered to submerge the transducers 16 into the liquid lens material 312. The lens material 312 is then allowed to cure, after which the probe 10, with the formed lens 26 attached to the transducers 14, are removed from the mold 310.

Figure 6:
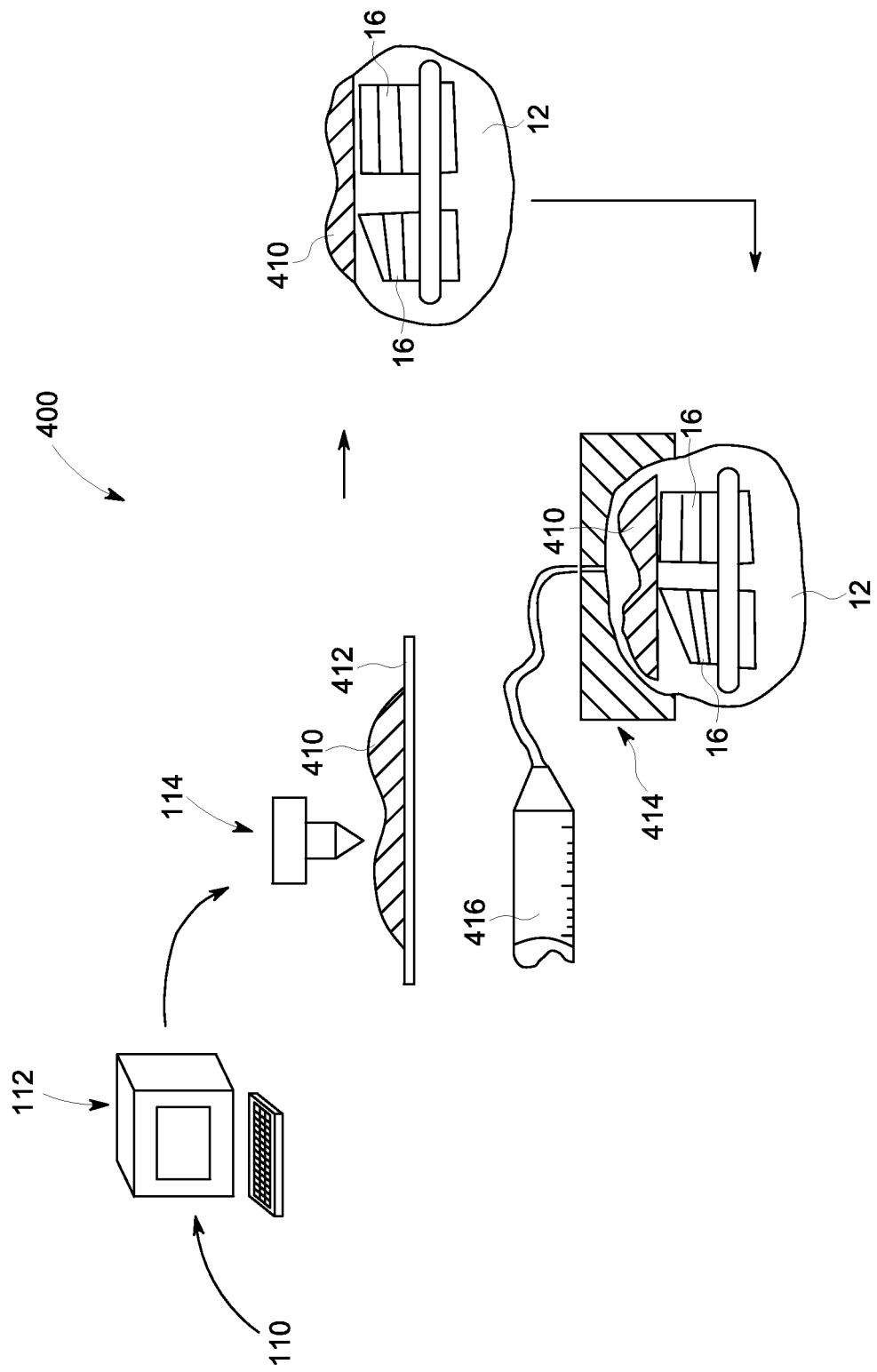
FIG. 6 is a schematic illustration of a system for manufacturing an ultrasound probe lens in accordance with another embodiment of the present invention.

Referring now to FIG. 6, a system 400 for manufacturing the custom lens 26 for the ultrasound probe 10 according to another embodiment of the present invention is illustrated. Like the systems 100, 300 described above, system 400 includes a laser mapping device 110, a data analyzer 112 and an additive manufacturing device 114. As described above, the laser mapping device 110 is configured to measure and map the surface profile of the transducers 16 of the acoustics 14 of the probe 10. The data analyzer 112 is configured to receive the surface profile data gathered by the laser mapping device 110 and to calculate the ideal curvature of the lens 26 for each probe 10 in the manner hereinbefore described. Once the ideal curvature is calculated, the data analyzer may output a step file (or other format file) to the additive manufacturing device 112.

Rather than printing the lens directly on the acoustic stack 14, however, the additive manufacturing device 114 of the system 400 is configured to print a custom lens 410 having the calculated surface profile/curvature on a substrate 412. After printing the lens 410, the substrate 412 may be removed from the lens 410 and the lens may then be tacked or bonded to the transducers 16 affixed in the housing 12 of the probe 10. This entire assembly is then placed in a mold 414 of a standard over-molding device that encapsulates the transducer assembly 16 and the custom printed lens 410, as illustrated in FIG. 6. A curable lens material is then injected into the mold 414 by an injection device 416 in an over-molding process to permanently bond the lens 410 in place and to seal the transducers 416. The curable lens material that is utilized to bond the lens 410 in place and to seal the assembly does not perform ad beam forming or focusing, but simply conforms to the lens 410.

In an embodiment, a method is provided. The method includes the steps of measuring a surface profile of a first component, determining a profile of a second component, the profile of the second component being configured to correspond to the surface profile of the first component, and manufacturing the second component utilizing additive technology in accordance with the determined profile. In an embodiment, the first component is a transducer of an ultrasound probe and the second component is a lens of the ultrasound probe. In an embodiment, the step of determining the profile of the lens includes calculating a curvature of the lens in dependence upon the measured surface profile of the transducer. In an embodiment, the method also includes the steps of aligning the transducer within a 3D printer and manufacturing the lens by printing the lens having the calculated curvature. In an embodiment, the method may also include the step of, after the lens is printed, verifying the curvature of the lens. In an embodiment, measuring the surface profile of the transducer is carried out utilizing a 3D laser scanning system. In an embodiment, the 3D laser scanning system may be configured to capture any variation of the transducer in x, y and z planes and to detect any rotation around the x, y and z axes. In an embodiment, the lens is comprised of a polymeric material. In an embodiment, prior to measuring the surface profile of the transducer, the transducer may be arranged within a housing of the ultrasound probe.

In an embodiment, a method of manufacturing a lens for an ultrasound probe is provided. The method includes the steps of measuring a surface profile of an acoustic stack of the probe, calculating a profile for the lens, and printing the lens onto the acoustic stack in accordance with the calculated profile. In an embodiment, the acoustic stack includes an array of transducers. In an embodiment, the step of determining the profile for the lens includes calculating a curvature of the lens in dependence upon the measured surface profile of the acoustic stack. In an embodiment, the method may also include the steps of aligning the probe within a 3D printer, and constructing the lens by printing the lens having the calculated curvature. In an embodiment, the method may also include verifying the curvature of the lens after the lens is printed. In an embodiment, measuring the surface profile of the transducer may be carried out utilizing a laser surface profilometer. In an embodiment, the laser surface profilometer is configured to capture any variation of the acoustic stack in x, y and z planes and to detect any rotation around the x, y and z axes. In an embodiment, the lens is comprised of a polymeric material.

In an embodiment, a system for manufacturing an ultrasound probe is provided. The system includes a laser mapping device configured to measure a surface profile of a transducer of the probe, a data analyzer configured to receive surface profile data from the laser mapping device and to calculate a profile for an acoustic lens in dependence upon the surface profile data, and an additive printing device configured to print an acoustic lens on the transducer in accordance with the calculated profile. In an embodiment, the laser mapping device is a laser surface profilometer. In an embodiment, the additive printing device is a 3D printer configured for polymer deposition.

In another embodiment, a method of manufacturing a lens for an ultrasound probe is provided. The method includes the steps of mapping a surface profile of a transducer of the ultrasound probe, determining a profile of the lens, the profile of the lens being configured to correspond to the surface profile of the transducer, manufacturing a mold having a mold profile corresponding to the determined profile of the lens, introducing a liquid material into the mold, submerging the transducer of the ultrasound probe in the liquid material, allowing the liquid material to cure to form the lens and removing the ultrasound probe and lens from the mold.

In yet another embodiment, a method of manufacturing a lens for an ultrasound probe is provided. The method includes the steps of measuring a surface profile of a transducer of the ultrasound probe, determining a profile of the lens, the profile of the lens being configured to correspond to the surface profile of the transducer, printing the lens on a substrate utilizing additive technology in accordance with the determined profile, removing the substrate from the lens, tacking the lens to the transducer of the ultrasound probe, over-molding the lens and the transducer with a curable material to bond the lens in place.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method of manufacturing a lens for an ultrasound probe, comprising the steps of:
   measuring a surface profile of an acoustic stack of the ultrasound probe;
   calculating a profile for the lens;
   printing the lens onto the acoustic stack in accordance with the calculated profile; and
   wherein the step of calculating the profile for the lens includes calculating a curvature of the lens in dependence upon the measured surface profile of the acoustic stack.

2. The method according to claim 1, wherein:
   the acoustic stack includes an array of transducers.

3. The method according to claim 1, further comprising the steps of:
   aligning the probe within a 3D printer; and
   constructing the lens by printing the lens having the calculated curvature.

4. The method according to claim 3, further comprising the step of:
   verifying the curvature of the lens after the lens is printed.

5. The method according to claim 4, wherein:
   measuring the surface profile of the acoustic stack is carried out utilizing a laser surface profilometer.

6. The method according to claim 5, wherein:
   the laser surface profilometer is configured to capture any variation of the acoustic stack in x, y and z planes and to detect any rotation around the x, y and z axes.

7. The method according to claim 1, wherein:
   the lens is comprised of a polymeric material.

* * * * *